US005792657A

United States Patent [19]

Gazdar et al.

[11] Patent Number: 5,792,657
[45] Date of Patent: Aug. 11, 1998

[54] STEROID SECRETING HUMAN ADRENOCORTICAL CARCINOMA CELL LINES

[75] Inventors: Adi F. Gazdar, Dallas, Tex.; Renato V. La Rocca, Louisville, Ky.; Cy A. Stein, New York, N.Y.; Charles E. Myers; Herbert K. Oie, both of Rockville, Md.

[73] Assignee: The United States of America as represented by the Department of Health and Human Services, Washington, D.C.

[21] Appl. No.: 486,679

[22] Filed: Jun. 7, 1995

Related U.S. Application Data

[63] Continuation of Ser. No. 308,502, Sep. 21, 1994, abandoned, which is a continuation of Ser. No. 92,923, Jul. 16, 1993, abandoned, which is a continuation of Ser. No. 558,552, Jul. 24, 1990, abandoned.

[51] Int. Cl.⁶ .............................. C12N 5/00; C12P 21/04; C12P 33/00; C12P 1/00
[52] U.S. Cl. .......................... 435/366; 435/363; 435/325; 435/70.1; 435/52; 435/41
[58] Field of Search ............................. 435/240.1, 240.2, 435/70.1, 366, 363, 325, 52, 41

[56] References Cited

PUBLICATIONS

A. Leibovitz, et al.; "Brief Communication: New Human Cancer Cell Culture Lines. I. SW-13, Small-Cell Carcinoma of the Adrenal Cortex", J. Natl. Cancer Inst. 51: 691–97 (1973).

B. Fang; PNAS, USA 74: 1067 (1977).

C. Moffett, Fed. Proc. 46: 648 (1987).

D. ATCC Catalogue of Cell Lines & Hybridomas, 6th ed. pp. 63–64 (1988).

E. Staels, et al.; "Regulation of Steroidogenesis in NCI-H295 Cells: A Cellular Model of the Human Fetal Adrenal" Mol. Endo 7(3): 423–433 (1993).

F. Rainey, et al.; "Regulation of Human Adrenal Carcinoma Cell (NCI-H295) Production of $C_{19}$ Steroids" J. Clin. Endo Metab 77(3): 731–737 (1993).

G. Bird, et al.; "Human NCI-H295 Adrenocortical Carcinoma Cells: A Model for Angiotensin–II Responsive Aldosterone Secretion" Endo 133(4): 1555–1561 (1993).

H. Murray, et al.; "Gap Junction Assembly and Endocytosis Correlated with Patterns of Growth in a Cultured Adrenocortical Tumor Cell (SW–13)" Cancer Res 41: 4063–4074 (Oct. 1981).

I. Alberts, et al.; Molecular Biology of the Cell pp. 335–339 (1983).

Primary Examiner—John W. Rollins
Assistant Examiner—Christopher R. Tate
Attorney, Agent, or Firm—Susan S. Rucker

[57] ABSTRACT

Continuous cell lines have been established from adrenocortical corcinomas. The cell lines are maintained in fully defined serum-free, steroid-free mediums. The cells of the invention, as exemplified by NCI-H295 cells, express all of the major pathways of steroid-ogenesis, including formation of corticosteroids, mineralocorticoids and androgens.

1 Claim, 9 Drawing Sheets

STEROID SECRETING HUMAN ADRENOCORTICAL CARCINOMA CELL LINES

This application is a is a continuation, of application Ser. No. 08/308,502, filed Sep. 21, 1994, now abandoned, which is a continuation of application Ser. No. 08/092,923, filed Jul. 16, 1993, now abandoned, which is a continuation of application Ser. No. 07/558,552, filed Jul. 24, 1990, now abandoned.

BACKGROUND OF THE INVENTION

1. Field of the Invention

The present invention relates to the establishment and characterization of permanent, functioning cultures of human adrenocortical carcinomas, maintained in fully defined serum-free, steroid-free mediums. In a specific embodiment, the invention relates to the continuous cell line, NCI-H295, which was established from an invasive primary adrenocortical carcinoma.

2. Background Information

Multiple pathways of steroidogenesis are present in the normal adrenal cortex, primarily involving formation of glucocorticoids, mineralocorticoids and weak androgens (Hall PF, Int. Rev. Cytol. 86:53, 1984; Nussdorfer GG, Cytophysiology of the Adrenal Cortex: International Review of Cytology Series, Vol. 98, Academic Press, Orlando, p 1, 1986). In addition, small amounts of estrogens are secreted, and some progesterone is produced as an intermediary in the formation of other steroids. One or more of the steroid pathways may be expressed by benign adenomas and malignant carcinomas of the adrenal cortex. The former are a common finding at autopsy, especially in the elderly, and most are non-functioning. In contrast, carcinomas are exceedingly rare neoplasms, whose incidence has been estimated to be 0.5 to 2 per million per year (Brennan MF, The Adrenal Gland, in DeVita VT, Hellman S Rosenberg SA (eds), Cancer: Principles and Practice of Oncology, J. B. Lippincott, Philadelphia, p. 1192, 1985; Cohn K, et al, Surgery 100:1170, 1986). Most carcinomas are functioning, with about 50% associated with Cushing's syndrome, 20% with virilization, 4% with both, 12% with feminization and 4% with hypermineralocorticoidism (due to hypersecretion of aldosterone or of other salt-retaining steroids; Cohn K, et al, Surgery 100:1170, 1986). Thus only about 10% of carcinomas are non-functioning, and even some of these may be associated with secretion of clinically inapparent precursor steroids such as pregnenolone or 17-hydroxypregnenolone.

The sex distribution of adrenocortical carcinomas is equal, although more women have functioning tumors. While the average age at presentation is 40 to 50 years, there is a broad spectrum. Many tumors are large (with a mean diameter of 16 cm) at presentation. Areas of cystic necrosis, hemorrhage, calcification, mitoses and local invasion are common. Seventy percent of carcinomas at presentation have extra adrenal spread or distant metastases, especially to the lungs and liver.

Cultures of the adrenal cortex offer useful models to study the biology of the various steroid pathways, including their hormonal control, inter-relationships, and secretion. Many studies have utilized short-term cultures of normal or neoplastic human adrenal cells for these purposes (Tazaki H, Invest. Urology 11:288, 1974; Higashijima M, et al, Endocrinol. Japan 34:635, 1987; Higashijima M, et al, Endocrinol. Japan 34:647, 1987; Matsuo K, et al., Acta Pathol. Japan 36:1659, 1986). However, the list of established, permanent cell lines established from human adrenocottical adenocarcinomas is remarkably short. A computerized search of the National Library of Medicine archives revealed citations of only three putative human cell lines. The SW-13 cell line was established by Leibovitz and coworkers in 1973 from an undifferentiated 'small cell' carcinoma of adrenal cortex (Leibovitz A, et al, J. Natl. Cancer Inst. 51:691, 1973). It is not known to secrete any steroid product. In 1977, Fang established a cell line that only secreted estrogen (Fang VS, Proc. Natl. Acad. Sci. USA 74:1067, 1977). A literature search conducted by the present inventors revealed only one further citation to this cell line by Furuhashi and Fang in 1980 (Furuhashi N, et al, Tohoku J. Exp. Med. 132:87, 1980.) In 1987, Moffett described, in abstract form (Moffett RB, Fed. Proc. 46:648, 1987), an adrenal tumor line that secreted renin and angiotensin. To date, this line has not been described in detail in the medical literature. Thus, none of the three human lines mentioned secrete any of the major steroid products of the normal adrenal cortex, and only one, SW-13, has been utilized by multiple investigators.

For lack of a suitable human model, many investigators have utilized the Y1 mouse line (Schimmer BP, The Adrenocortical Tumor Cell Line, Y1, in Sato G (ed), Functionally Differentiated Cell Lines, Alan Liss, New York, p. 61, 1981) cultured by Sato and coworkers from a serially transplanted tumor that arose many years previously in a mouse exposed to radiation. However, the Y1 line has properties unusual in human adrenocortical carcinomas, including ACTH mediated control of steroidogenesis, growth and morphology.

SUMMARY OF THE INVENTION

The present invention relates to continuous cell lines established from adrenocortical carcinomas. The cell lines can be established in a fully defined medium, for example HITES, and later adapted for growth in a simple medium. The simple medium can be supplemented, for example, with selenium, insulin and transferrin, and can be devoid of serum, steroids, fibroblast growth factor and a source of exogenous cholesterol. In a specific embodiment, the invention is directed to the cell line, NCI-H295, which was established from an invasive primary adrenocortical carcinoma.

The cells of the invention, as exemplified by NCI-H295 cells, have the ultra-structural features of steroid secreting cells, and contain complex cytogenetic abnormalities including the presence of multiple marker chromosomes. Multiple pathways of steroidogenesis are expressed by the present cells, including formation of corticosteroids, mineralocorticoids and androgens.

The cell lines of the invention are expected to be useful in studying the regulation, metabolic pathways and enzymes involved in steroid formation and secretion. In addition, the present cell lines are expected to be useful as models for testing therapeutic modalities for adrenocortical carcinoma.

3

Figure 3:
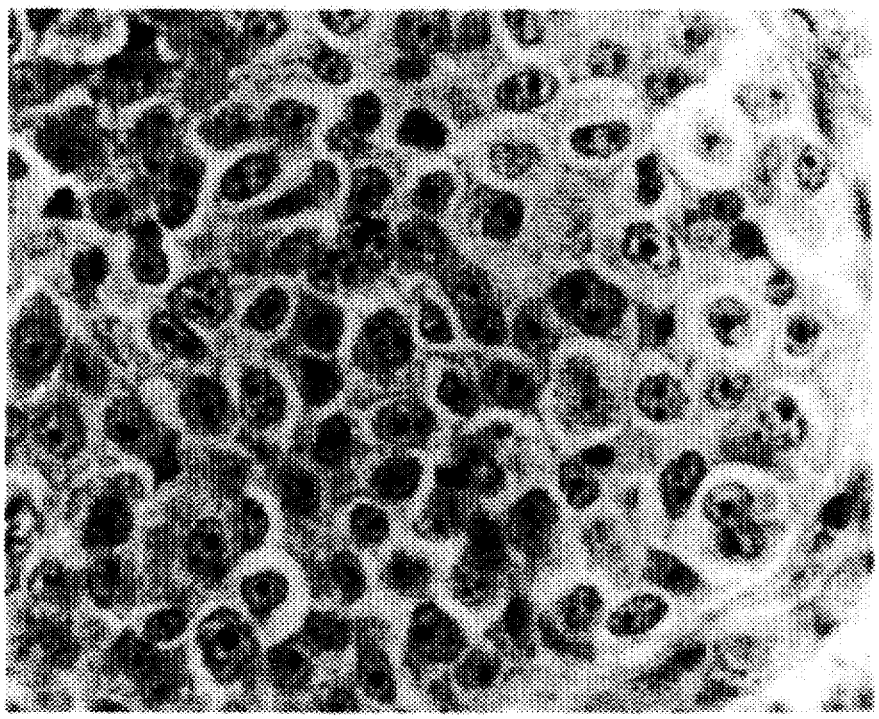

FIG. 3. Histological appearances of xenograft induced by subcutaneous inoculation of NCI-H295 cells into an athymic nude mouse. The appearances of the xenograft are similar to those of the original adrenocortical carcinoma, although there are fewer multinucleated and bizarre appearing cells.

Figure 4:
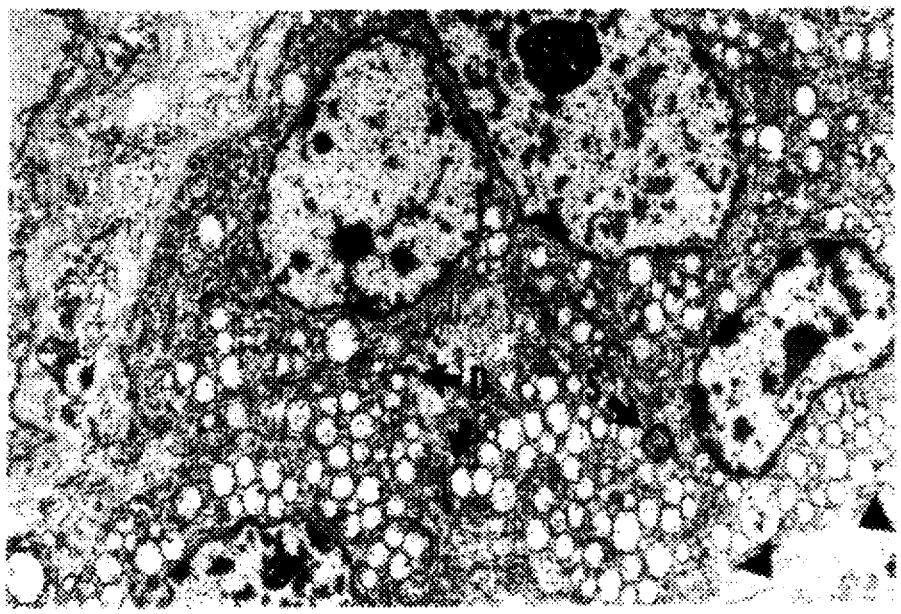

FIG. 4. Ultrastructural appearance of the original tumor. Portions of four nuclei, one with a conspicuous nucleolus, are obvious within epithelioid cells. Large numbers of cytoplasmic mitochondria with cleared (autolyzed) cristae are evident. Less conspicuous is the vesicular endoplasmic reticulum between the mitochondria. A single structure resembling a spironolactone body is present in one cell (S), indicative of the steroidogenic character of the tumor cells, especially in context with the above features. Other features include cell to cell attachments typical of epithelia (desmosomes, D), and discontinuous basal lamina (all arrow heads).

Figure 5:
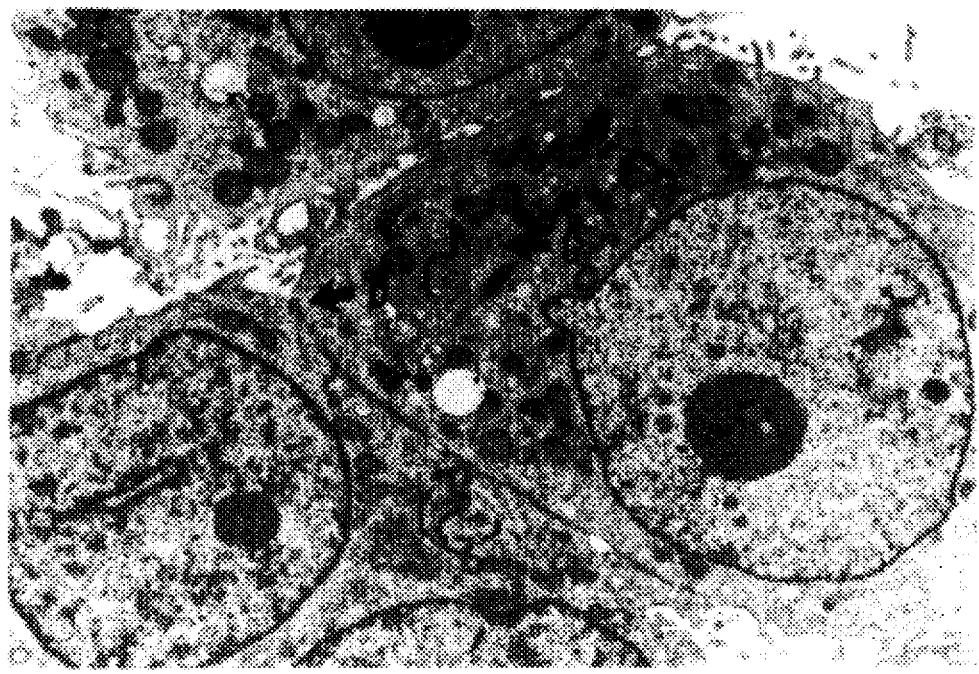

FIG. 5. Ultrastructural appearances of the cell line, NCI-H295, derived from the tumor described in FIG. 4. The cells remain epithelioid, with desmosomes (D), and nucleoli remain prominent. Overall preservation is much better, and the numerous mitochondria are more apparent. Prominent Golgi apparatus is obvious as well (G). Features of in vitro cultured cells present include absence of basal lamina, and numerous microvilli.

Figure 6A:
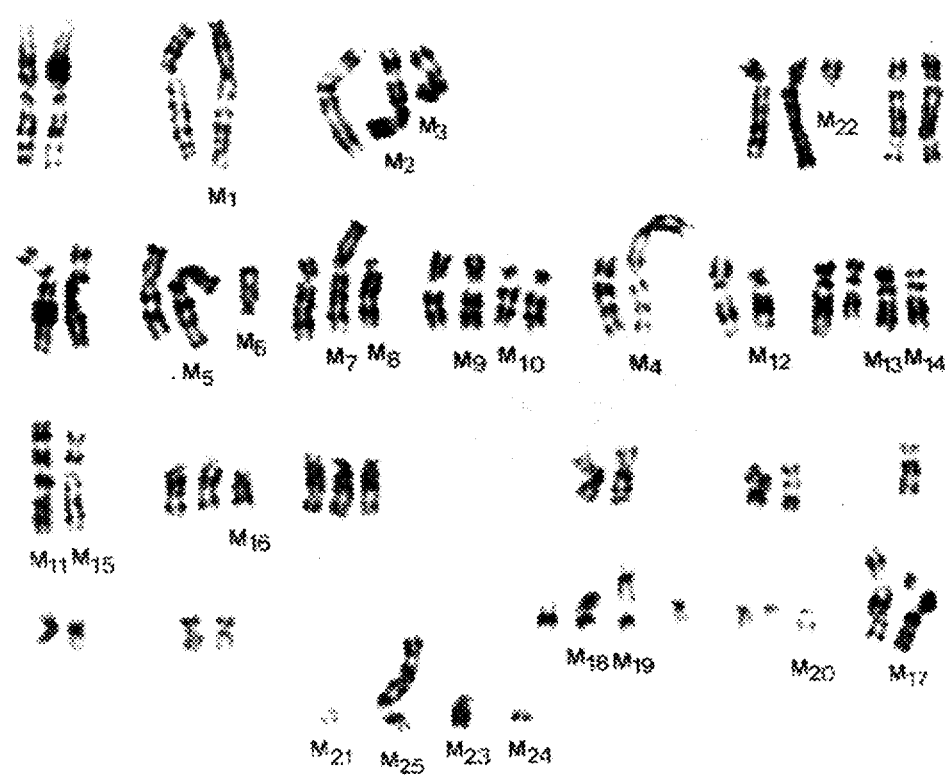

FIG. 6A. Trypsin-G banded karyotype from the major subline of NCI-H295. The 25 common marker chromosomes are numbered. Marker chromosome 12 is deletion 11p.

Figure 6B:
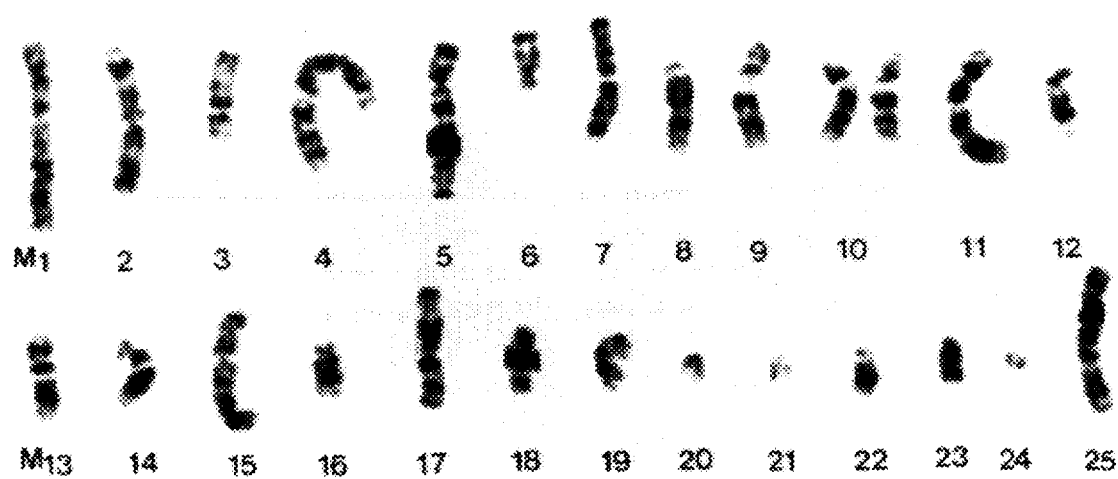

FIG. 6B A set of marker chromosomes from another cell. They are identified by the number preceded by the letter M on the extreme left in each row.

Figure 7:

FIG. 7. A trypsin-G banded metaphase spread from the minor subline showing its unique chromosome pattern, i.e., the presence of del(M5)(p11) (M26, arrow) and der(17)t (17;?)(q25;?) (M27, arrow), and the single copy of N17 (arrow head). The lack of M5 of the major subline should be noted (FIG. 5). Otherwise, both sublines have nearly identical chromosome composition. The other common markers are identified by the number corresponding to that shown in FIG. 6A.

Figure 8:
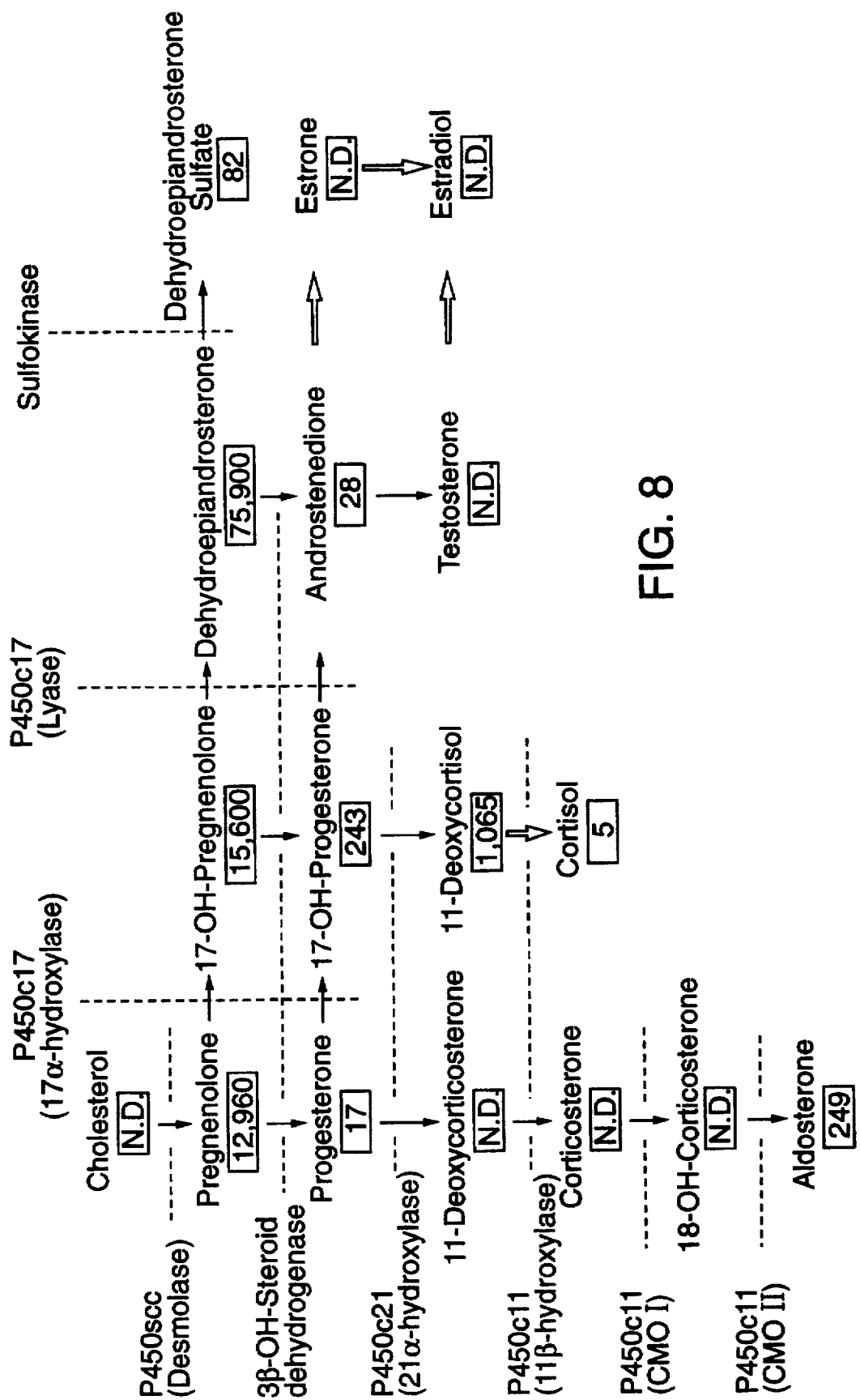

FIG. 8. Steroid secretion by NCI-H295 cells cultured in serum supplemented SIT medium (SIT-2), as determined by RIA. The major pathways of adrenal cortical steroidogenesis are outlined.

The open arrows indicate reactions that occur predominantly in peripheral tissues. The enzymes involved are indicated in the left and upper columns, and the corresponding reaction or reactions are indicated by dashes. The boxed-in figures contain the values (in ng/million cells/24 hr) of the steroid products mentioned above present in the supernatant fluids of the cultured cells (mean values of two experiments performed with cells grown in HITES medium). N.D.=not done.

Figure 9:
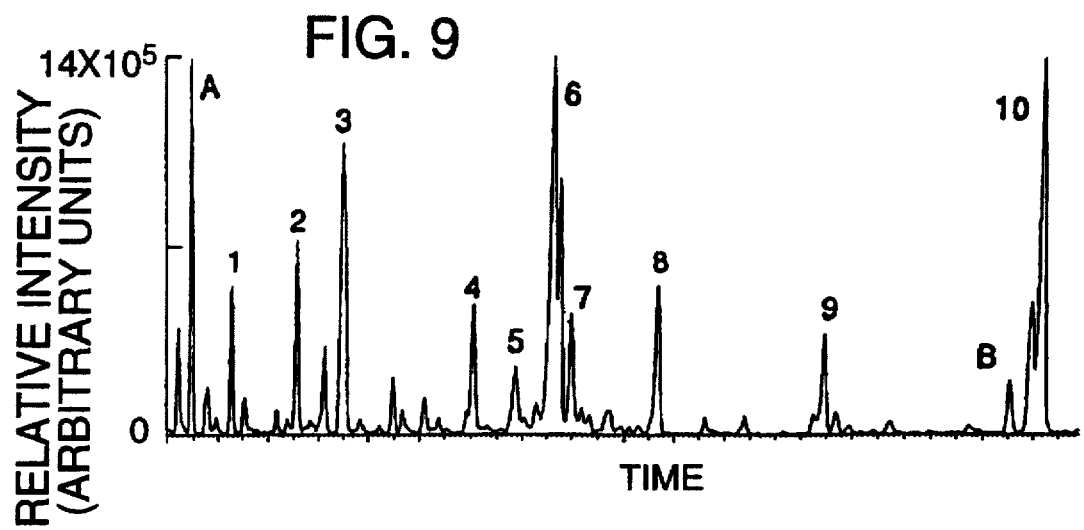

FIG. 9. GC/MS chromatographic analysis of methyloxime-trimethylsilyl esters of steroids performed in serum supplemented medium. The 10 most prominent peaks are labelled numerically and identified in Table 1 below. For certain components, two peaks are present, due to separation of the syn and anti-forms of the oxime derivative. Peaks A and B are internal standards.

Figure 10:
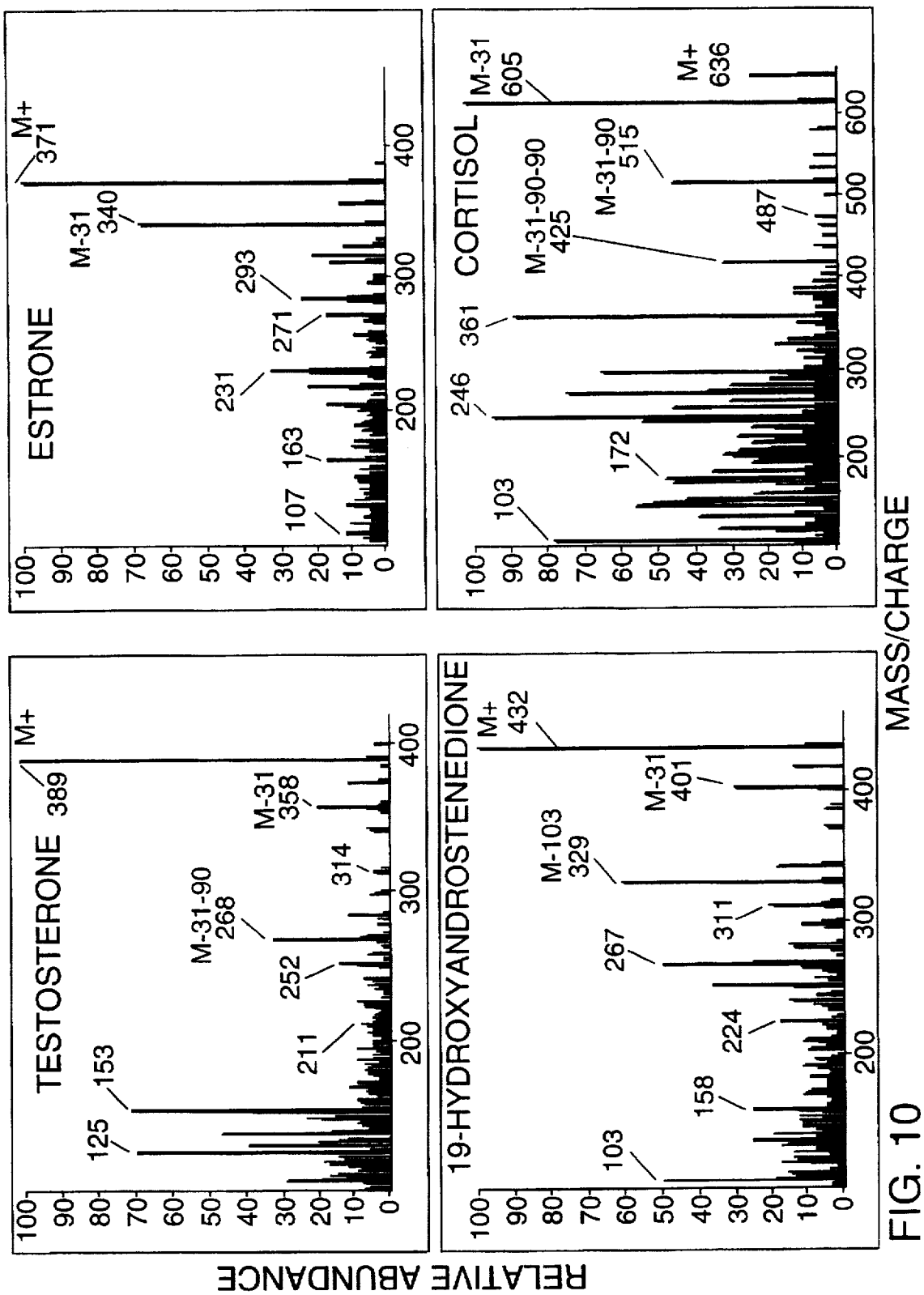

FIG. 10. Representative mass spectra of methyloxime-trimethylsilyl esters of steroids identified by GC/MS analysis. Similar results were obtained for all the other steroids listed in Table 1 below. In all cases the mass spectra were identical to those of corresponding reference compounds.

Figure 11:
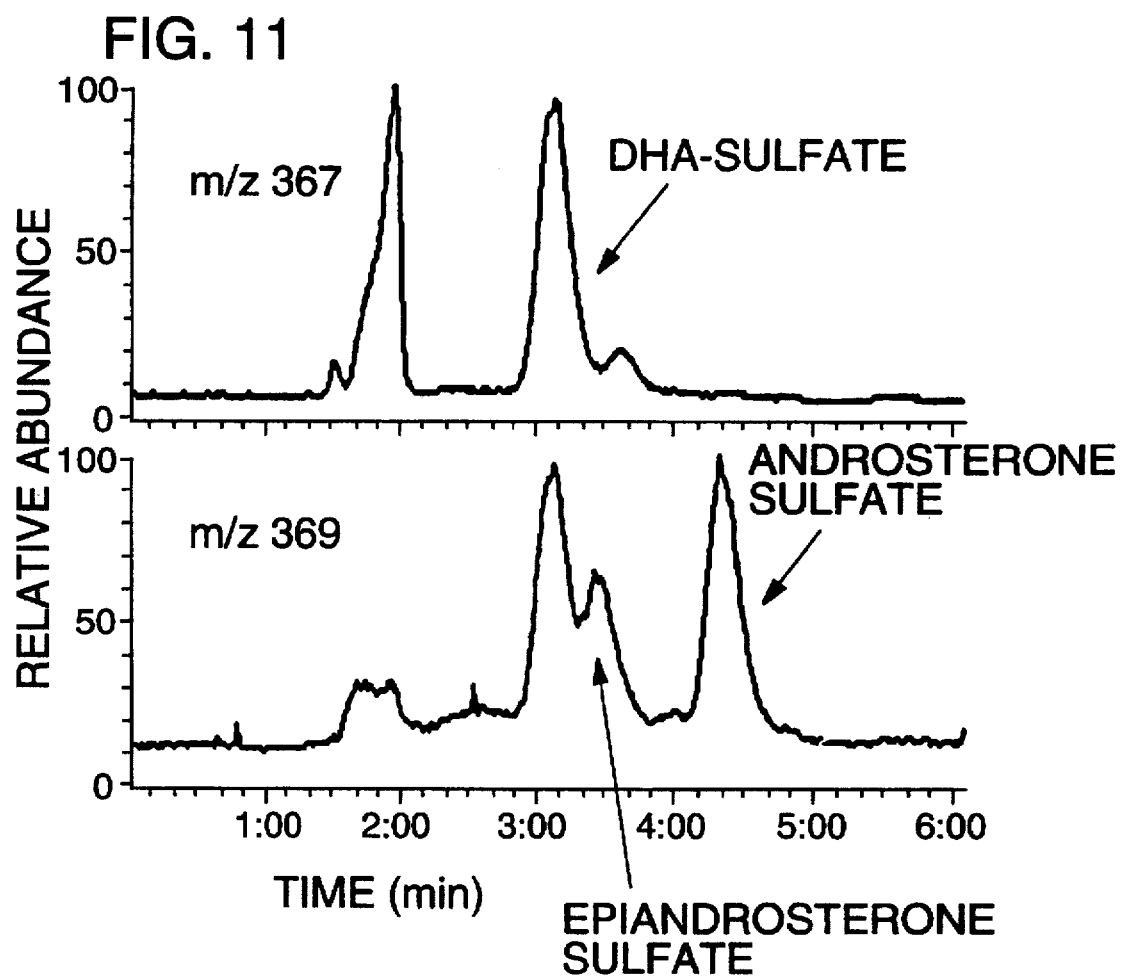

FIG. 11. Negative ion selected-ion monitoring of secreted androgen sulfates (m/z 367 and m/z 369) by thermospray HPLC/MS. The early component in the m/z 367 illustration was not identified, but may be testosterone sulfate or 3α-hydroxy-5-androsten-17-one sulfate.

DETAILED DESCRIPTION OF THE INVENTION

The present invention is directed to continuous cell lines established from adrenocortical carcinomas.

In one embodiment, the invention is directed to cell cultures consisting essentially of adrenocortical carcinoma cells that secrete steroids characteristic of adrenocortical cells.

In another embodiment, the invention relates to a method of establishing cell cultures consisting essentially of adrenocortical carcinoma cells that secrete steroids characteristic of adrenocortical cells, comprising the steps of: (i) culturing populations of cells derived from an adrenocortical carcinoma in fully defined serum-free medium that includes selenium, insulin and transferrin; and (ii) selecting the adrenocortical carcinoma cells.

In still another embodiment, the invention relates to a method of determining the ability of an agent to affect growth of adrenocortical carcinoma cells, comprising: (i) culturing adrenocortical carcinoma cells that secrete steroids characteristic of adrenocortical cells in the presence of a pharmaceutically acceptable amount of the agent under conditions such that in the absence of the agent, proliferation of the cells of step (i) would be effected; and (ii) determining the effect of the agent on proliferation of the cells of step (i).

The cell lines can be established in a fully defined medium, for example HITES, and later adapted for growth in a simple medium. The simple medium can be supplemented, for example, with selenium, insulin and transferrin, and can be devoid of serum, steroids, fibroblast growth factor and a source of exogenous cholesterol. In a specific embodiment, the invention relates to NCI-H295 cells. ATCC Accession No. CRL 10296 NCI-H295 cells were deposited at the American Type Culture Collection on Nov. 13, 1989, located at 12301 Parklawn Drive, Rockville, Md. 20852, under the terms of the Budapest Treaty. NCI-H295 cells have a relatively long population doubling time, and are tumorigenic when inoculated subcutaneously into athymic nude mice.

The cells of the invention, as exemplified by NCI-H295 cells, have the ultrastructural features of steroid secreting cells, and contain complex cytogenetic abnormalities including the presence of multiple marker chromosomes. Steroid studies on NCI-H295 cells performed nearly seven years after culture initiation have demonstrated secretion of multiple steroids characteristic of adrenocortical cells, including very high concentrations of pregnenolone, 17-hydroxypregnenolone, and dehydroepiandrosterone, modest concentrations of 17-hydroxyprogesterone, aldosterone and 11-deoxycortisol, and trace amounts of progesterone, androstenedione, and dehydroepiandrosterone sulfate. Thus, multiple pathways of steroidogenesis are expressed by the cells of the invention, including formation of corticosteroids, mineralocorticoids and androgens, and these pathways are stably retained by the cells after many years in culture.

The patient from whom cell line NCI-H295 was established had, in many ways, the typical clinical, biochemical and pathological profile of adrenocortical carcinoma (Brennan MF, The Adrenal Gland, in DeVita VT, Hellman S, Rosenberg SA (eds), Cancer: Principles and Practice of Oncology, Lippincott JB, Philadelphia, p. 1192, 1985; Brennan MF, CA - A Journal for Physicians 37:348, 1987). She was 48 years old, presented with a large, locally invasive malignant tumor which later metastasized to the lungs and liver, and she had clinical and biochemical evidence of excessive secretion of glucocorticoids, and ketosteroids. However, she also had hyperaldosteronism, a relatively rare finding in association with adrenocortical carcinoma.

The ability of the present inventors to establish in continuous culture a functioning adrenocortical carcinoma, e.g. the NCI-H295 cell line, when many others have failed, is believed to be due to the use of a fully defined medium, such as HITES, originally formulated for the growth of small cell carcinoma of the lung (Simms E, et al., Cancer Res. 40:4356, 1980; Carney DN, et al, Proc.

Natl. Acad. Sci. USA 78:3185, 1981). Initial tumor cell growth in conventional serum containing medium was unsuccessful due to fibroblast overgrowth, although the culture could be adapted to growth in such medium once it became established in serum free medium. Initial or continued growth of the cell lines of the invention did not require fibroblast growth factor, a potent stimulator of normal and cultured adrenocortical cells (Gospodarowicz D, et al, Endocrin. 100:1080, 1977; Simonian MH, et al, Endocrin. 111:919, 1982). Short term culture of bovine adrenocortical cells can be achieved in a fully defined medium supplemented with selenium, insulin, transferrin, lipoproteins, albumin, fibroblast growth factor, and vitamins (Simonian MH, et al, Endocrin. 111:919, 1982). The cells of the invention could be adapted to growth in a simple medium supplemented only with selenium, insulin and transferrin. These findings indicate that the present cells may secrete autocrine growth factors. Of interest, SW-13 cells are reported to secrete as yet unidentified autocrine growth factors (Halper J, et al, Cancer Res. 43:1972, 1983).

The ultrastructural features of steroid secreting cells include the characteristic appearance of mitochondrial cristae (lamellar or tubulovesicular) and the presence of a well developed smooth endoplasmic reticulum (Nussdorfer GG, Cytophysiology of the Adrenal Cortex: International Review of Cytology Series, Vol. 98, Academic Press, Orlando, p. 1, 1986; Ghadially FN, Adrenals, in Ghadially FN (ed), Diagnostic Electron Microscopy of Tumours, Butterworths, Boston, p. 291, 1985). These features reflect the subcellular location of the enzymes involved in steroidogenesis, and they were present in both the tumor and cultured cells. Lipid droplets are a prominent feature of adrenocortical cells, especially in species in which most of the cholesterol is derived from lipoproteins (Nussdorfer GG, Cytophysiology of the Adrenal Cortex: International Review of Cytology Series, Vol. 98, Academic Press, Orlando, p. 1, 1986). Lipid droplets were inconspicuous in, for example, NCI-H295 cells, most likely reflecting the entirely endogenous production of cholesterol requirements (described below).

Cytogenetic studies demonstrated a highly aneuploid line containing multiple marker chromosomes, 25 of which were common to most cells, although a minor subpopulation was noted (FIGS. 6 and 7). However, karyotypes of individual cells were remarkably similar. The inventors found only two reports of cytogenetic studies on human adrenocortical tumors. In a functioning carcinoma, Limon et al. (Cancer Genet. Cytogenet. 28:343, 1987) found abnormalities involving only chromosomes 4 and 11. However, in a non-functioning carcinoma, they found several marker chromosomes (Limon J, et al, Cancer Genet. Cytogenet. 26:271, 1987). In addition, the inventors have performed cytogenetic studies of the non-functioning human adrenocortical carcinoma cell line SW-13.

Despite the relative paucity of cytogenetic studies in human adrenocortical carcinomas and cell lines, certain common features are noted. Chromosomes 1, 7, 9, 14, 16, and 20 had contributed to the formation of marker chromosomes in three of the four adrenocortical carcinomas examined. Among the marker chromosomes in these three carcinomas, N7 had the highest incidence, involving 14 markers; N14 and N20 involved 8 markers; and N9 and N12 involved 7 markers. While most of the break-union sites, including those involving N7, occurred pericentrically, 7q36 was a break-union site noted in two different carcinomas (NCI-H295 and the non-functioning carcinoma; Limon J, et al, Cancer Genet. Cytogenet. 26:271, 1987). Of interest, frequent structural abnormalities of N7 also are characteristic of cell lines derived from colorectal carcinomas, melanomas and gliomas (Mark J, et al, Hereditas. 87:243, 1977; Chen TR, J. Natl. Cancer Inst. 61:277, 1978; Chen TR, et al, Cancer Genet. Cytogenet. 6:93, 1982), and 7q36 is a frequent break-union site in colon carcinomas.

The major function of the adrenal cortex is to produce biologically active steroids (some of which are converted to their final products in other organs). The cortex produces more than 40 different steroids (Nussdorfer GG, Cytophysiology of the Adrenal Cortex: International Review of Cytology Series, Vol. 98, Academic Press, Orlando, p 1, 1986; Neville AM, et al, The Human Adrenal Gland, Springer-Verlag, New York, 1982). Both glucocorticoids and mineralocorticoids have 21 carbon atoms, and are uniquely produced by the cortex. The cortex is also a major source of $C_{19}$, androgens and a minor source of $C_{16}$ estrogens and progestins. The initial and final steps in steroidogenesis occur in the mitochondria and the intermediate ones in the smooth endoplasmic reticulum. The major events in steroidogenesis are briefly outlined below and in FIG. 8, and related to steroid secretion by the cells of the invention, as exemplified by NCI-H295 cells.

All of the adrenal steroids are derived from cholesterol. The major source of adrenal cholesterol (about 80%) in humans is plasma cholesterol esters derived from circulating lipoproteins (Nussdorfer GG, Cytophysiology of the Adrenal Cortex: International Review of Cytology Series, Vol. 98, Academic Press, Orlando, p 1, 1986; Higashijima M, et al, Endocrinol. Japan 34:635, 1987; Higashijima M, et al, Endocrinol. Japan 34:647, 1987). In addition, endogenous formation occurs from acetate. Presumably, the cells of the invention are capable of synthesizing all of the cholesterol required for steroidogenesis, because steroid synthesis occurred in fully defined, serum-free, cholesterol-free medium.

Conversion of cholesterol to pregnenolone in the mitochondria is the rate limiting step in normal adrenal steroid biosynthesis. The side chain cleavage desmolase complex, consisting of a reaction-specific cytochrome $P_{450}$, cleaves the side chain from the 27 carbon cholesterol molecule to form a 21 carbon molecule that functions as the steroid skeleton. The relatively high concentrations of pregnenolone secreted by NCI-H295 cells indicates that it is formed at a faster rate than it can be metabolized.

Pregnenolone is transported to the smooth endoplasmic reticulum where it is converted to progesterone by 3β-hydroxysteroid dehydrogenase-isomerase complex. Cortisol synthesis proceeds via 17α-hydroxylation of pregnenolone to form 17α-hydroxyprogesterone which, in turn, is converted by 21-hydroxylation to 11-deoxycortisol. This compound is further hydroxylated in the mitochondria by 11β-hydroxylase to cortisol, the principal glucocorticoid. Glucocorticoid formation occurs almost exclusively in the zona fasciculata. Aldosterone, the principal mineralocorticoid, is also formed from progesterone, in the zona glomerulosa, by sequential 21- and 11β-hydroxylation via corticosterone and 18-hydroxycorticosterone. The production of adrenal androgens requires prior 17α-hydroxylation, and thus does not occur in the zona glomerulosa. The major quantitative production of androgens is by conversion of 17α-hydroxypregnenolone to the $C_{19}$ steroids dehydroepiandrosterone and its sulfated conjugate. The other major adrenal androgen, androstenedione, is produced from 17α-hydroxyprogesterone. It can be converted (mainly in other tissues) to testosterone as well as to estrogens. NCI-H295 cells secrete relatively large quantities of the major adrenal androgens, and smaller amounts of testosterone and estradiol.

These findings indicate that the major pathway of pregnenolone metabolism in NCI-H295 cells is androgen formation, although mineralocorticoids and glucocorticoids are also synthesized. In many adrenocortical carcinomas, secretion of the end products of the various steroid pathways (cortisol, aldosterone, androstenedione and dehydroepiandrosterone sulfate) is modest, because 11β-hydroxylase activity is decreased or absent (O'Hare MJ, et al, Human Pathol. 10:137, 1979). Cortisol and corticosterone formation was demonstrated in NCI-H295 cells by GC/MS, and aldosterone formation by RIA. These findings indicate the presence in NCI-30 H295 cells of all of the major adrenocortical enzyme systems, including 11β-hydroxylase, desmolase, 21α-hydroxylase, 17α-hydroxylase, lyase and sulfokinase. The differences in the formation of the $C_{21}$ end products by the two assay methods (performed more than one year apart) suggest shunting between mineralocorticoid and glucocorticoid pathways. Of interest, the two assay methods revealed very similar results for secretion of dehydroepiandrosterone in SIT-2 medium.

Steroid storage granules have not been unequivocally demonstrated in adrenocortical cells, and the precise mechanism of hormone release is controversial. The most widely accepted theory for hormone release is that they freely diffuse throughout the cytosol and plasma membrane (Nussdorfer GG, Cytophysiology of the Adrenal Cortex: International Review of Cytology Series, Vol. 98, Academic Press, Orlando, p 1, 1986). However, a more complex mechanism involving active transport has also been postulated (Nussdorfer GG, Cytophysiology of the Adrenal Cortex: International Review of Cytology Series, Vol. 98, Academic Press, Orlando, p 1, 1986; Raven PW, et al, J. Endocr. 99:13, 1983). That steroid storage in NCI-H295 cells was not demonstrated in spite of considerable extracellular concentrations favors the freely diffusible theory.

The cell lines of the invention, as exemplified by the NCI-H295 cell line, continue to secrete multiple steroids even after many years in culture, and when grown in a fully defined medium, devoid of steroids, serum and fibroblast growth factor. The present cell lines are expected to prove useful in studying the regulation, metabolic pathways and enzymes involved in steroid formation and secretion.

In another embodiment, the spontaneous production by the present cell lines of various steroid and steroid precursor hormones, especially culture media lacking "expensive" fetal calf serum, is expected to allow collection of significant quantities of steroid products. In addition, various biologic manipulations are expected to allow preferential production of specific steroids by the cell lines.

In a further embodiment, the cell lines of the invention are expected to serve as the ideal in vitro test to assay the effect of any adrenal steroid hormone inhibiting agent (aminogluthemide-like agents).

In still another embodiment, the cell lines of the invention are expected to be useful in the isolation and characterization of enzymes involved in steroid formation and secretion. As all of the major pathways of steroidogenesis are represented in the cells, by inference, all of the major enzymes required for steroid synthesis must be present in the cells.

In a further embodiment, the cells of the invention are expected to be useful in the study of growth factors relating to the adrenal cortex. Because the cells can be cultured in a relatively simple fully defined medium, the cells produce many of the growth factors required. These factors may be isolated from the supernatant fluids of growing cultures.

In yet another embodiment, the invention is expected to be useful as a model to test new therapeutic modalities for adrenocortical carcinoma. In vitro testing of putative new chemotherapeutic agents are frequently performed prior to clinical studies. Thus, the present cells may be used for the selection of new drugs and other therapeutic modalities for adrenocortical carcinoma.

The following non-limiting example illustrates the invention in more detail.

EXAMPLE 1

ESTABLISHMENT OF THE NCI-H295 CELL LINE

Methodology

Cell culture establishment and characterization: Finely minced tissue, selected from viable, non-hemorrhagic portions of a primary adrenocortical carcinoma were cultured in 96 well microplates containing growth medium. Four media were utilized, RPMI-1640 or Dulbecco's modified medium supplemented with 10% fetal bovine'serum (R10 medium and D10 respectively), RPMI-1640 medium supplemented with hydrocortisone, insulin, transferrin, 17β-estradiol, and sodium selenite (HITES medium), which was originally formulated for the selective culture of small cell lung carcinoma (Simms E, et al, Cancer Res. 40:4356, 1980; Carney DN, et al, Proc. Natl. Acad. Sci. USA 78:3185, 1981), and HITES medium supplemented with 2% fetal bovine serum (H2 medium). Because HITES medium contains two steroids, for steroid secretion studies cells were cultured in RPMI-1640 medium supplemented with sodium selenite, insulin and transferrin (SIT) and 2% serum (SIT-2) or without serum (SIT-0).

Ultrastructural studies of tumor tissue and cultured cells were performed as previously described (Green WR, et al, Ultrastruct. Pathol. 6:141, 1984).

For confirmation of tumorigenicity, $5 \times 10^6$ cultured cells were inoculated subcutaneously into athymic nude mice (Gazdar AF, Int. J. Cancer 28:777, 1981). Xenografts so induced were examined by light microscopy after formalin fixation.

Cytogenetic methods: Slides for cytogenetic studies were prepared by the standard air-dry method from exponentially growing cultures after colcemid treatment (0.1 µg/ml final concentration for 45 min.). They were stained with the fast G-banding (Chen TR, Mamm. Newsl. 22:70, 1981) for detailed chromosome analysis, and with quinacrine mustard for sex determination by fluorochrome observation. Chromosome number distribution was assessed from 100 metaphyses, and the percentage of cells having ploidies higher than the modal chromosome number estimated by scanning 500 metaphyses.

Steroid Analyses

Radioimmunoassays (RIAs): Methodology and validation of steroid analyses using radioimmunoassay after column chromatography have been previously described (Schiebinger RJ, et al, J. Clin. Endocrin. Metabol. 62:202, 1986; Ito T, et al, J. Clin. Endocrin. Metabol. 34:106, 1972; Cutler GB, et al, Endocrin. 103:2112, 1978; Abraham GE, et al, Anal. Letters 5:757, 1972; Abraham GE, et al. J. Clin. Endocrin. Metabol. 32:619, 1971; Glass AR, et al, Fert. Steril. 30:560, 1978; Kao M, et al, Chem. 21:1644, 1975). The results were analyzed by logit-log analysis using a computer program.

Mass spectrometry (MS): Data obtained from RIAs were confirmed and extended by MS analyses, either gas chromatography/MS (GC/MS) or HPLC/MS. While the separation and identification of steroids by MS has been reviewed by Shackleton (Endocr. Rev., 6:441, 1985), because of the complexity and multiple permutations of these methods, the ones utilized in the present studies are described in detail. Steroids were extracted from 500 ml samples representing pooled 24 hours harvests. Steroids were extracted using Sep-pak cartridges Shackleton CH, et al, Clin. Chim. Acta, 107:231, 1980) from Waters Assoc., Milford, MA. Because the volumes were large, the cartridges were eluted with methanol prior to extraction of further 50 ml aliquots. Following extraction, the methanol eluates were dried under vacuum and reconstituted in 4 ml methanol. To a portion of the steroid extracts was added three internal standards (5α-androstane-3α, 17α-diol, stigmasterol and cholesteryl butyrate), and methyloxine derivatives were made of reactive carbon groups. For some steroids, particularly sensitive selected-ion monitoring methods were used, with the crude extract fractionated by Sephadex LH-20 prior to derivatization (Setchell KD, et al, Clin. Chim. Acta, 47:381, 1973). For GC/MS, samples were separated on a 15 m SPB-1 fused-silica capillary column attached to a Hewlett-Packard 5970 mass spectrometer. The samples, dissolved in cyclohexane, were injected splitless with oven temperature 50° C. This temperature was held for 3 min and the oven then rapidly taken up to its starting temperature of 230° C. The temperature was programmed to 310° C. at 2°/min. Mass spectra were obtained by repetitive scanning over the 100-800 amu mass range. Intact steroid sulfates present in the extract were also analyzed by thermospray HPLC/MS. Separation was achieved on a 15 cm C18 column housed in a Waters 600 instrument using the solvent system methanol, 70:0.1 M ammonium acetate (O'Hare MJ, et al, Human Pathol. 10:137, 1979). The eluent for the HPLC passed through a thermospray interface to a VG 30-250 mass spectrometer. Negative ion mass spectra of the separated components were obtained. The androgen sulfates were further analyzed by negative ion selected ion monitoring of their molecular anions.

Results

Figure 1:
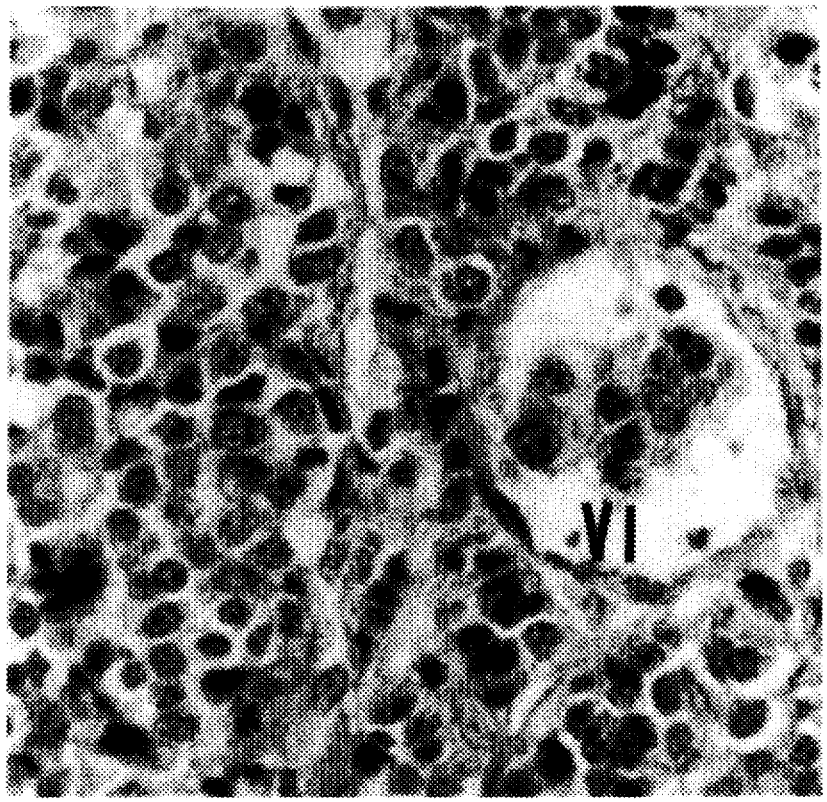
FIG. 1. Adrenocortical tumor from which cell line NCI-H295 was cultured. The cells are relatively small and uniform, although occasional cells are multinucleated and bizarre appearing. Vascular invasion is present.

Case history: The patient, a 48 year old black woman from the Bahamas, was evaluated in October 1980 for weight loss, acne, facial hirsutism, edema, diarrhea, and recent cessation of menses. CAT scan revealed a large adrenal mass. She was referred to the National Cancer Institute, Bethesda, Maryland. Her serum cortisol was 11.9 µg/dl, and her 24 hour urine excretion levels of cortisol, aldosterone, and 17-ketosteroids were greatly elevated, while her 17-hydroxycorticoids urine levels were near the upper limit of normal (but they failed to suppress with dexamethasone). In December 1980, a 14×13×11 cm right adrenal mass was removed surgically. The tumor had the histological appearances typical of a malignant adrenocortical carcinoma (O'Hare M. J., et al, Human Pathol. 10:137, 1979), including abundant eosinophilic cytoplasm, and large oval to round nuclei with prominent nucleoli. Many mitoses, pleomorphic cells, and foci of necrosis were present, as well as invasion of perinephric fat and vascular channels, indicative of the highly malignant nature of this tumor (FIG. 1). In February 1981, her tumor recurred and multiple bilateral pulmonary nodules were noted, of which 16 were removed by thoracotomy. She was treated with mitotane and cortisone acetate. In September 1981, further pulmonary nodules and hepatic filling defects were noted. She returned to the Bahamas, and died a few months later.

Pathological examination of the adrenal tumor revealed an invasive, necrotic adrenocortical carcinoma, with mitoses and large bizarre cells. The pulmonary lesions were similar in appearance. Electron microscopic examination of the adrenal mass demonstrated features typical of steroid secreting cells.

Figure 2:
FIG. 2. Phase contrast photomicrograph of NCI-H295 cells cultured in RPMI-1640 medium supplemented with 10% fetal bovine serum. The cells are adherent, and epithelioid and spindle shaped. In HITES and SIT media, the cells grew as floating cell aggregates lacking substrate attachment.

Establishment and characterization of NCI-H295 cell line: A portion of the adrenal tumor was finely minced and placed in culture in microwells with one of four growth media. Initial growth, at a slow rate, occurred in all four media. In R10 and D10 media, fibroblast overgrowth of the tumor cells eventually occurred, and the cultures were discarded. In HITES medium, 'pure' tumor cell growth as floating aggregates occurred. In H2 medium, tumor cells grew as both floating and adherent colonies. However, because a few adherent fibroblasts also were present, the floating cells were selected for passage. After about a year, the HITES culture was determined to be the most vigorous, and was the only one selected for continuous propagation. After establishment, the cells could readily be adapted to culture in R10 medium. In HITES medium (which is devoid of attachment factors), the cells grow as floating aggregates of loosely aggregated cells, while in R10 medium they grow as attached epithelioid or spindle shaped cells (FIG. 2). Most of the characterization studies described herein were performed in HITES medium.

Five of six athymic nude mice inoculated subcutaneously with $5 \times 10^6$ NCI-H295 cells developed tumors at the inoculation site six to nine weeks later. The xenografts so induced had histological appearances similar to the adrenocortical carcinoma present in the patient (FIG. 3) although bizarre, multinucleated cells were more common in the tumor.

Ultrastructural studies: Electron microscopic study of the tumor and the cell line established from it confirmed the steroidogenic character of both (Nussdorfer GG, Cytophysiology of the Adrenal Cortex: International Review of Cytology Series, Vol. 98, Academic Press, Orlando, p 1, 1986; Ghadially FN, Adrenals, In Ghadially FN (ed), Diagnostic Electron Microscopy of Tumours, Butterworths, Boston, p 291, 1985). The original tumor cells (FIG. 4), though suffering moderate autolytic damage, were characterized by enormous numbers of mitochondria (with artifactually lysed cristae), vesicular smooth endoplasmic reticulum, epithelioid nuclei with prominent nucleoli, and even rare cytoplasmic structures resembling spironolactone bodies, found only in adrenal cortical cells. Epithelial cell to cell attachments were noted. Basal lamina also were present, though widely disrupted, a feature more characteristic of carcinoma as opposed to adenoma cells.

The cultured tumor cells, even from late passages, clearly retained many of the same, features noted above (FIG. 5). In particular, the nuclei remained clearly epithelioid, with single prominent nucleoli; the cytoplasm contained large numbers of mitochondria (without autolytic changes), moderate vesicular smooth endoplasmic reticulum, and prominent Golgi apparatus, features typical of secretory activity. The latter feature was less conspicuous in the original cells, perhaps masked by the widespread autolytic changes noted above. Cell to cell attachments, like in the original tumor, remained conspicuous. Basal lamina (a feature usually lacking in cultured cells) were no longer present. Microvilli, a feature characteristic of cultured epitheloid cells, were quite prominent.

Cytogenetic studies: Cytogenetic examination of NCI-H295 revealed a hypertriploid human cell line with the modal chromosome number, 62, occurring in 30 of 100 cells counted. The distribution of chromosome numbers was as follows:

| Number of Cells | 3 | 2 | 5 | 4 | 12 | 17 | 15 | 30 | 10 | 2 |
|---|---|---|---|---|---|---|---|---|---|---|
| Number of chromosomes | 55 | 56 | 57 | 58 | 59 | 60 | 61 | 62 | 63 | 64 |

The rate of higher ploidies was 3.8%. No Y or Y-like chromosomes were found by fluorescent microscopy.

Karyotypic analysis of 38 cells demonstrated a total of 65 marker chromosomes. Of these, 25 were common to most cells (FIGS. 6a and b). Two subline specific markers occurred in some cells (FIG. 6b), and the remaining 38 were detected only once. Most of the break-union sites occurred pericentrically, although one was noted at 7q36.

A minor subline occurred in about 16% of cells. This subline possessed, instead of der(7)t(7;7)(q36;p13) (or M5) and the paired N17 seen in karyotypes of the major subline, two new markers, del (M5) (7p11) (or M26) and der(17)t (17;?)(q25;?) (or M27), and the single N17 (FIG. 7). All other chromosomes were identical, otherwise. Neither double minutes nor heterogeneously staining regions were detected. Normal N13 was absent. N15 and N22 constantly had three and four copies per cell, respectively. Other normal chromosomes (either one or two copies per metaphase) were present in over 90% of cells.

Steroid secretion: Steroid studies were performed after the cells had been in culture for 7–10 years. RIA analyses of clarified supernatant fluids of the cells cultured in SIT medium (with or without 2% bovine serum) contained varying concentrations of several steroids characteristic of adrenocortical cells (FIG. 8). In particular, very high concentrations of pregnenolone, 17-hydroxypregnenolone, and dehydroepiandrosterone were present, along with more modest concentrations of 17-hydroxyprogesterone, aldosterone and 11-deoxycortisol, and trace amounts of progesterone, androstenedione, and dehydroepiandrosterone sulfate. Cortisol concentrations were below those that could be detected with confidence. Unused culture media, and spent media of control lung adenocarcinoma cells (grown in HITES medium) lacked detectable levels of these steroids. Dehydroepiandrosterone and 17-hydroxyprogesterone were not detected in cell pellet homogenates of NCI-H295 cells.

GC/MS assays demonstrated the presence of more than 30 steroids when the cells were cultured in serum containing medium (SIT-2), of which about 20 were identified. The 10 major steroids, listed in Table 1 below, accounted for greater than 70% of the total, and the separation of these is illustrated in FIG. 9. Representative mass spectra of methyloxime-trimethylsilyl ether derivatives are illustrated in FIG. 9. These, and all other mass spectra were identical to those of equivalent reference compounds, and the peaks had the same retention times. No steroids were identified in control samples of the two media. The presence of the sulfated steroids, dehydroepiandrosterone sulfate, epi-androsterone sulfate and androsterone sulfate were detected by thermospray HPLC/MS (FIG. 10). Certain expected steroids were not identified by MS, including progesterone, deoxycorticosterone, 18-hydroxycorticosterone and aldosterone. Particularly sensitive selected-ion monitoring methods were used to no avail in the search for these compounds. Because serum supplemented media contain cholesterol and a mixture of steroids, the studies also were performed in serum free SIT medium (Table 1 below). Cell growth in SIT-0 medium was considerably slower than in SIT-2 medium. The population doubling time of the cells was considerably longer in SIT-0 than in SIT-2 medium. The total concentration of secreted steroids was decreased about four-fold in SIT-0 medium (Table 1 below), and $C_{21}$ steroid formations was greatly decreased relative to $C_{19}$ steroid formation (Table 1 below). RIA assays confirmed that a considerable decrease in steroid secretion occurred in SIT-0.

TABLE 1

The Major Steroids Present in Supernatant Fluids of NCI-H295 Cells Cultured in Serum-Containing and Serum Free Media, as Identified by GC/MS.

| Steroid | % of total | |
|---|---|---|
| | SIT-2* | SIT-0** |
| Cortisol (peak 10) | 21.3 | 0.6 |
| 11β-hydroxyandrostenedione (peak 6) | 15.9 | 4.6 |
| Androstenedione (peak 3) | 11.7 | 6.8 |
| 5-Pregnene-3β,17α,20α-triol (peak 8) | 5.1 | 3.6 |
| Dehydroepiandrosterone (peak 2) | 4.5 | 11.0 |
| Pregnenolone (peak 5) | 3.4 | 3.5 |
| 5-androstene-3(α),16α,17β-triol (peak 4) | 3.4 | 3.5 |
| 17α-hydroxypregnenolone (peak 7) | 3.3 | 4.8 |
| 3α-hydroxy-5-androsten-17-one (peak 1) | 3.0 | 1.8 |
| 11-deoxycortisol (Compound S) (peak 9) | 2.6 | <1.5 |
| Total steroid secretion (/$10^6$ cells/24 hr) | 2.83 μg | 0.72 μg |

*SIT-2: SIT medium supplemented with 2% fetal bovine serum.
**SIT-0: Serum free SIT medium.

Of more than 30 steroids identified by GC/MS in serum containing medium, the relative percentages of the 10 most abundant are listed in Table 1. The peak numbers correspond to the peaks illustrated in FIG. 9. In addition to the above-listed steroids, the following were identified, none of them representing more than 3% of the total: androsterone, epiandrosterone, testosterone, 17α-hydroxyprogesterone, estrone, 16α-hydroxyDHA, 18-hydroxyandrostenedione, 16α-hydroxypregnenolone, corticosterone, estradiol and 5-androstene-3β,16α, 17β-triol. Several other steroids remain unidentified including at least two hydroxyandrostenediones, and an important X,18-dihydroxyandrostenedione. The sulfated forms of androgens identified by HPLC/MS (see above) are not included in this Table.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit of and scope of the invention.

What is claimed is:

1. An isolated cell line, NCI-H295, which is designated as ATCC CRL-10296.

* * * * *